(12) United States Patent
Goldfarb et al.

(10) Patent No.: US 7,618,774 B2
(45) Date of Patent: Nov. 17, 2009

(54) MATERIALS AND METHODS FOR IDENTIFYING GENES AND/OR AGENTS THAT ALTER REPLICATIVE LIFESPAN

(75) Inventors: David S. Goldfarb, Victor, NY (US); Michael Breitenbach, Salzburg (AT)

(73) Assignee: University of Rochester, Rochester, NY (US)

( * ) Notice: Subject to any disclaimer, the term of this patent is extended or adjusted under 35 U.S.C. 154(b) by 556 days.

(21) Appl. No.: 10/790,456

(22) Filed: Mar. 1, 2004

(65) Prior Publication Data

US 2004/0265861 A1 Dec. 30, 2004

Related U.S. Application Data

(60) Provisional application No. 60/451,309, filed on Feb. 28, 2003, provisional application No. 60/468,467, filed on May 6, 2003.

(51) Int. Cl.
*C12Q 1/68* (2006.01)
*C12N 1/16* (2006.01)
*C12N 1/18* (2006.01)

(52) U.S. Cl. .................. 435/6; 435/254.2; 435/254.21; 435/254.22

(58) Field of Classification Search ........................ None
See application file for complete search history.

(56) References Cited

U.S. PATENT DOCUMENTS 5,874,210 A * 2/1999 Guarente et al. ............... 435/4
6,200,746 B1 * 3/2001 Fisher et al. .................... 435/5
6,228,583 B1 5/2001 Guarente et al.
6,531,289 B1 * 3/2003 Bradley et al. ............. 435/7.31

OTHER PUBLICATIONS

Jazwinski, S.M. An Experimental System for the Molecular Analysis of the Aging Process: The Budding Yeast *Saccharomyces cerevisiae*, Journal of Gerontology 45(3):B68-74, 1990.*
Minois, N. How Should We Assess the Impact of Genetic Changes on Ageing in Model Species? Ageing Research Reviews 5:52-59, 2006.*
Jarolim, S. et al. A novel assay for replicative lifespan in *Saccharomyces cerevisiae* FEMS Yeast Research 5:169-177, 2004.*
Bobola et al., "Asymmetrical Accumulation of Ash1p in Postanaphase Nuclei Depends on a Myosin and Restricts Yeast Mating-Type Switching to Mother Cells," *Cell* 84:699-709 (1996).
Jarolim et al., "Is There a Way to Select For Long Lived Yeast Mutants?" at 1st International Meeting of Yeast Apoptosis, Braga, Portugal (Oct. 4-6, 2002) retrieved from the internet at http://www.bio.uminho.pt/imya/html/ab8.htm.

* cited by examiner

*Primary Examiner*—Nancy Vogel
(74) *Attorney, Agent, or Firm*—Nixon & Peabody LLP

(57) ABSTRACT

Recombinant materials, including DNA constructs, expression vectors, and host cells, and methods of identifying an environmental stimulus or a gene that alters the lifespan of an organism are identified. The recombinant DNA constructs include first and second chimeric genes that both encode substantially the same protein that is required for yeast replication, the first chimeric gene containing a promoter responsive to growth medium conditions and the second chimeric gene containing a promoter operable in mother cells but not daughter cells.

8 Claims, 2 Drawing Sheets

SEQUENCE LISTING

```
<160> NUMBER OF SEQ ID NOS: 4

<210> SEQ ID NO 1
<211> LENGTH: 628
<212> TYPE: DNA
<213> ORGANISM: Artificial Sequence
<220> FEATURE:
<223> OTHER INFORMATION: Description of Artificial Sequence: GAL1/10
      bi-directional promoter

<400> SEQUENCE: 1
ttatattgaa ttttcaaaaa ttcttacttt tttttggat ggacgcaaag aagtttaata         60
atcatattac atggcattac caccatatac atatccatat ctaatcttac ttatatgttg        120
tggaaatgta aagagcccca ttatcttagc ctaaaaaaac cttctctttg gaactttcag        180
taatacgctt aactgctcat tgctatattg aagtacggat tagaagccgc cgagcgggcg        240
acagccctcc gacggaagac tctcctccgt gcgtcctcgt cttcaccggt cgcgttcctg        300
aaacgcagat gtgcctcgcg ccgcactgct ccgaacaata aagattctac aatactagct        360
tttatggtta tgaagaggaa aaattggcag taacctggcc ccacaaacct tcaaattaac        420
gaatcaaatt aacaaccata ggatgataat gcgattagtt ttttagcctt atttctgggg        480
taattaatca gcgaagcgat gattttgat ctattaacag atatataaat ggaaaagctg         540
cataaccact ttaactaata ctttcaacat tttcagtttg tattacttct tattcaaatg        600
tcataaaagt atcaacaaaa aattgtta                                           628

<210> SEQ ID NO 2
<211> LENGTH: 1400
<212> TYPE: DNA
<213> ORGANISM: Artificial Sequence
<220> FEATURE:
<223> OTHER INFORMATION: Description of Artificial Sequence: HO
      promoter

<400> SEQUENCE: 2
gttaaaagtt acatcctttt tttcattttt ccctacgctc agggcactgt actgcccgtg         60
cctgcgatga gatacatcaa tttaaaaaaa aaaccagcat gctataatgc tggagcaaaa        120
```

-continued

```
atttcaatca gaaatagaaa agacctcaac agtaattaac ccaaaggggt atcaaataat      180
cgatgtgctt tttcactcta cgaatgatct gtgagaaact gatttgggcc gaatcgcgta      240
aaaagtttga ttcgtggcgg ctaatgtctg aggggctcca acaggctcgt agagcctcgt      300
ttcttgaggg cacaaaatgt ccaggtaata ttcccaagaa agaaccgcag agtgctttga      360
taaatcggtt acaggtctta acgtaggttt tgtctcgcta attgctattg agtaagttcg      420
atccgtttgg cgtcttttgg ggtgtaacgc caaacttatt acttttccta tttgaggttg      480
gtattgattg ttgtcaaaga atgaaaatat acacaaacgc cacaatatac gtaccaggtt      540
cacgaaaact gatcgtatgg ttcatacect gacttggcaa acctaatgtg accgtcgctg      600
attagcggat cacgaaaagt gatctcgata caattagagg atccacgaaa atgatgtgaa      660
tgaatacatg aaagattcat gagatctgac aacatggtag acgtgtgtgt ctcatggaaa      720
ttgatgcagt tgaagacatg tgcgtcacga aaaagaaat caatcctaca cagggcttaa       780
gggcaaatgt attcatgtgt gtcacgaaaa gtgatgtaac taaatacacg attaccatgg      840
aaattaacgt acctttttg tgcgtgtatt gaaatattat gacatattac agaaagggtt       900
cgcaagtcct gtttctatgc ctttctctta gtaattcacg aaataaacct atggtttacg      960
aaatgatcca cgaaaatcat gttattattt acatcaacat atcgcgaaaa ttcatgtcat     1020
gtccacatta acatcattgc agagcaacaa ttcattttca tagagaaatt tgctactatc     1080
acccactagt actaccattg gtacctacta ctttgaattg tactaccgct gggcgttatt     1140
aggtgtgaaa ccacgaaaag ttcaccataa cttcgaataa agtcgcggaa aaaagtaaac     1200
agctattgct actcaaatga ggtttgcaga agcttgttga agcatgatga agcgttctaa     1260
acgcactatt catcattaaa tatttaaagc tcataaaatt gtattcaatt cctattctaa     1320
atggctttta tttctattac aactattagc tctaaatcca tatcctcata agcagcaatc     1380
aattctatct atactttaaa                                                 1400
```

<210> SEQ ID NO 3
<211> LENGTH: 179
<212> TYPE: DNA
<213> ORGANISM: Artificial Sequence
<220> FEATURE:
<223> OTHER INFORMATION: Description of Artificial Sequence:  cytochrome
      c transcription terminator

<400> SEQUENCE: 3

```
agatccgctc taaccgaaaa ggaaggagtt agacaacctg aagtctaggt ccctatttat       60
ttttttatag ttatgttagt attaagaacg ttatttatat ttcaaatttt tctttttttt      120
ctgtacagac gcgtgtacgc atgtaacatt atactgaaaa ccttgcttga aaggttttt      179
```

<210> SEQ ID NO 4
<211> LENGTH: 1542
<212> TYPE: DNA
<213> ORGANISM: Saccharomyces cerevisiae

<400> SEQUENCE: 4

```
atgtcagcta taccaataac tccaactaag cgtatcagaa gaaatctatt tgacgatgct       60
ccagcaacgc ctccacgacc tttgaaaaga aaaaagttgc agttcacaga tgttacacca      120
gaatcatccc cagaaaaact gcagtttggc tcacagtcta ttttttgag acaaaggca       180 cttttgcaga agtcatctga gctagtcaac ttgaatagca gcgatggtgc attgccagca      240
agaacagcag agtacgaaca agttatgaat tttttggcga aggcaatttc tgaacacagg      300
```

-continued

```
tccgattcac tgtacatcac gggtccgcct ggcactggca agactgccca gcttgatatg    360
attataagac agaagttcca gtccctccca ttgtcgctct ccacgccacg ctcgaaggac    420
gtgctgagac atacgaatcc gaacttgcag aatttgtcct ggtttgaatt gcccgatgga    480
aggctagaat ccgtggcggt aaccagtatt aattgtatat cgttgggaga gccgtcctcc    540
attttccaga agattttcga ttccttccaa gatctgaatg gcccaacatt gcaaataaaa    600
aacatgcagc atctacagaa gttcttagag ccttatcata agaaaactac gtttgtggtt    660
gtgttggacg agatggacag gctattgcat gctaacacga gcgagacaca atcagttaga    720
actattcttg aattattcct tttggcgaaa ttgcctactg tgagttttgt gttaatcggt    780
atggctaata gtctagatat gaaagatagg tttctttcca ggttaaattt ggacagaggg    840
ttgttaccgc aaactatagt ttttcagcca tacactgctg agcaaatgta tgaaatcgtc    900
attcaaaaaa tgagtagtct gcccactatt atcttccaac cgatggccat caaattcgca    960
gcaaagaagt gtgctggaaa tacgggtgac cttcgaaaac tttttgatgt cttaagggga   1020
agtatcgaaa tctatgagtt agaaaagcgg tttctgcttt caccaacaag aggatcattg   1080
aactctgcgc aagttccttt gacgccaact acttctccgg taaagaaatc gtatccagaa   1140
ccacaaggta aaataggctt gaactacata gccaaggtct tctcaaaatt cgtgaacaat   1200
aattctacga gaacgaggat agccaaacta aacatccagc aaaaattaat tctttgcacc   1260
ataattcaat cactgaagct aaattccgat gctacaatcg acgaatcgtt tgatcattat   1320
atcaaagcga taacaaaaac tgatacttta gcaccattgc agagaaatga attttggaa   1380 atctgtacaa ttttagaaac ttgtgggctg gtttcaatca aaaagacaaa gtgtaaaggg   1440
aaaaccaaga gatttgttga taagattgat gttgatctcg acatgcgaga attttatgat   1500
gagatgacca aaatttcaat tttgaaacct ttccttcact ag                      1542
```

MATERIALS AND METHODS FOR IDENTIFYING GENES AND/OR AGENTS THAT ALTER REPLICATIVE LIFESPAN

This application claims the benefit of U.S. Provisional Patent Applications Ser. Nos. 60/451,309 filed Feb. 28, 2003, and 60/468,467 filed May 6, 2003, each of which is hereby incorporated by reference in its entirety.

FIELD OF THE INVENTION

The present invention relates to recombinant materials, kits, and screening assays for identifying genes that influence and/or agents that alter replicative lifespan.

BACKGROUND OF THE INVENTION

There is now good evidence for the early appearance in evolution of conserved pathways for aging. These signaling pathways allow animals to postpone reproduction in unfavorable environmental conditions (Kenyon, "A Conserved Regulatory System for Aging," *Cell* 105:165-168 (2001); Tissenbaum et al., "Model Organisms as a Guide to Mammalian Aging," *Dev. Cell* 2:9-19 (2002)). Several elements of the signaling pathways and their related processes occur in *S. cerevisiae*, and provide a strong rationale for the use of yeast as a model genetic system for studying aging. For example, the phenomenon of caloric restriction is conserved as both rodents and yeast live longer when their 'diets' are restricted. Importantly, the genetic and molecular basis for the extended lifespan of organisms on low calorie diets is still poorly understood. In fact, it is still not known if the issue is low total calories or low carbon source, or some combination of nutrients. The conservation of these longevity mechanisms is consistent with the existence of other, yet undiscovered, mechanisms for the control and maintenance of health and/or reproductive capacity during an extended lifespan.

The effect of caloric restriction on lifespan in flies and worms is potentiated by the insulin growth factor pathway. Several homologous or analogous components of this pathway are conserved in yeast and also function in caloric restriction. The yeast protein kinase A (CRY1/PKA) signaling pathway responds to high glucose levels. CRY1/PKA mutants sporulate spontaneously in rich medium, and, significantly, increase both replicative and chronological lifespans (reviewed in Longo et al., "Evolutionary Medicine: From Dwarf Model Systems to Healthy Centenarians?" *Science* 299: 1342-1346 (2003)). The yeast SCH9 gene is homologous to worm and mammalian Akt kinases, and also functions in yeast aging (Fabrizio et al., "Regulation of Longevity and Stress Resistance by Sch9 in Yeast," *Science* 292:288-90 (2001)). These glucose-sensing pathways, when mutated or down regulated, increase lifespan. In yeast, these pathways involve nonessential components of G-protein Ras signaling (Jazwinski, "The RAS Genes: A Homeostatic Device in *Saccharomyces cerevisiae* Longevity," *Neurobiol. Aging* 20:471-478 (1999); Jazwinski, "Growing Old: Metabolic Control and Yeast Aging," *Annu. Rev. Microbiol.* 56:769-792 (2002)), and subunits of protein kinase, adenylase cyclase, and cAMP phosphodiesterase (Lin et al., "Enhanced Gluconeogenesis and Increased Energy Storage As Hallmarks of Aging in *Saccharomyces cerevisiae*," *J. Biol. Chem.* 276:36000-36007 (2001)).

Oxidative stress has been proposed as having a significant effect on lifespan. Down regulation of glucose signaling pathways also increases oxidative stress resistance by mechanisms dependent on conserved genes, including superoxide dismutase and catalase. Superoxide dismutase and catalase normally promote growth and increase protection against oxidative stress, and the mutation of these genes in yeast decreases replicative lifespan. Tied into these pathways are genes controlling the mitochondrial retrograde response pathway (Jazwinski, "New Clues to Old Yeast," *Mech. Age. Develop.* 122:865-882 (2001)). The disruption of the glucose signaling pathways in yeast increases lifespan by a SIR2-dependent mechanism (Longo et al., "Evolutionary Medicine: From Dwarf Model Systems to Healthy Centenarians?" *Science* 299:1342-1346 (2003)). Sir2p is a $NAD^+$-dependent histone deacetylase that acts to regulate lifespan downstream of the glucose-response signaling pathways. The role of Sir2p in aging may be regulated by the cellular concentration of $NAD^+$ or NADH (or their ratio), and/or nicotinamide, which rises under conditions of caloric restriction (Anderson et al., "Nicotinamide and PNC1 Govern Lifespan Extension by Calorie Restriction in *Saccharomyces cerevisiae*," *Nature* 423:181-185 (2003); Gallo et al., "Nicotinamide Clearance by Pnc1 Directly Regulates Sir2-mediated Silencing and Longevity," *Mol. Cell. Biol.* 24:1301-1312 (2004); Lin et al., "Calorie Restriction Extends Yeast Life Span by Lowering the Level of NADH," *Genes Dev.* 18:12-16 (2004)).

Downstream of the primary glucose response signaling pathways are numerous effectors that affect yeast lifespan. Two examples are the yeast RecQ-like helicase genes, WRN and SGS1 (Guarente et al., "Genetic Pathways That Regulate Aging in Model Organisms," *Nature* 408:255-262 (2000)). SGS1 is homologous to the human Werner syndrome gene, WRN, which causes a recessive disorder characterized by premature aging, and Bloom syndrome (BS) gene, which causes a recessive disorder characterized by short stature, and immunodeficiency. The human BS gene rescues the short lifespan of sgs mutant yeast cells, a fact which supports the conservation of lifespan mechanisms between yeast and humans (Heo et al., "Bloom's Syndrome Gene Suppresses Premature Aging Caused by Sgs1 Deficiency in Yeast Genes," *Cells* 4:619-625 (1999)).

One consequence of aging in *S. cerevisiae* is the accumulation of extrachromosomal rDNA circles (sometime called ERCs). rDNA circles are produced by gratuitous recombination among the 100-200 tandemly repeated rDNA genes, and are maintained because they happen to contain an origin of replication. The accumulation of rDNA circles is due to age-related 'genome instability', a catch-all phrase for various recombination and replication errors and miscues that occur in older cells. The accumulation of rDNA circles is an especially striking and readily quantified example of age-related genomic instability (Sinclair et al., "Extrachromosomal rDNA Circles—A Cause of Aging in Yeast," *Cell* 91:1033-1042 (1997)). rDNA circle accumulation requires SIR2 and is blocked by mutations in FOB1 (Guarente, "Sir2 Links Chromatin Silencing, Metabolism, and Aging," *Genes. Dev.* 14:1021-1026 (2000); Jazwinski, "New Clues to Old Yeast," *Mech. Age. Develop.* 122:865-882 (2001)). It is not certain that the accumulation of rDNA circles is a direct cause of aging or, alternatively, is consequence of defects in repair and replication systems that lead, for example, to increased mutation rates in older mother cells (McMurray et al., "An Age-Induced Switch to a Hyper-Recombinational State," *Science* 301:1908-11 (2003)).

Lifespan in yeast has been measured in two ways, chronological age and replicative age (Jazwinski, "Metabolic Mechanisms of Yeast Aging," *Exp. Gerontol.* 35:671-676 (2000)). Chronological age is the length of time that cells can survive in stationary phase, and replicative aging is the number of times a mother cell can produce a daughter cell before she senesces. Chronological and replicative aging in yeast are related, for example, because events in stationary phase affect subsequent replicative lifespan in rich medium (Longo et al., "Evolutionary Medicine: From Dwarf Model Systems to Healthy Centenarians?" *Science* 299:1342-1346 (2003); Ashrafi et al. "Passage Through Stationary Phase Advances Replicative Aging in *Saccharomyces cerevisiae*," *Proc. Natl. Acad. Sci. USA* 96:9100-9105 (1999)). Although there are merits to both types of aging assays, cells nearing the end of their replicative lifespan exhibit evidence of functional senescence, which may be more relevant to metazoan aging (Jazwinski, "Growing Old: Metabolic Control and Yeast Aging," *Annu. Rev. Microbiol.* 56:769-792 (2002)).

Current replicative aging assays involve counting the number of daughter cells produced by a cohort of about 40 individual mother cells placed in a grid on solid medium. This assay is tedious and usually requires close attention for 1-2 weeks. It would be desirable to identify a new assay that can quantify replicative aging in a straightforward high throughput assay.

Although, as noted above, a number of yeast genes and corresponding human homologs have been identified, there remains a need to identify other genes that affect lifespan. Moreover, to the extent that certain lifespan genes are associated with disease, it is desirable to provide an assay that can be used quickly and reliably to screen putative therapeutic agents to determine their efficacy in treating or minimizing the effects of such disease.

The present invention is directed to overcoming these and other deficiencies in the art.

SUMMARY OF THE INVENTION

A first aspect of the present invention relates to a method of identifying an environmental stimulus or a gene that alters the lifespan of an organism. The method is carried out by: providing a control cell culture and one or more test cultures, wherein the one or more test cell cultures but not the control cell culture comprise either (i) mother yeast cells that possess a genotype modification of either a non-essential gene or an essential gene (i.e., in a non-lethal manner), (ii) mother yeast cells that are exposed to an environmental stimulus other than a pro-oxidant, or (iii) mother yeast cells that possess a genotype modification of either a non-essential gene or an essential gene and are exposed to an environmental stimulus other than a pro-oxidant; culturing the control cell cultures and one or more test cell cultures under conditions whereby mother yeast cells can replicate and daughter yeast cells cannot; and determining whether the mother yeast cells in the one or more test cell cultures exhibit a change in replicable lifespan when compared to the mother yeast cells in the control cell culture, wherein an increase in the replicable lifespan for mother yeast cells of a test cell culture indicates that the genotype modification, the environmental stimulus, or the combination thereof, enhances the replicable lifespan of the mother yeast cells in the test cell culture.

A second aspect of the present invention relates to a DNA construct including first and second chimeric genes that both encode substantially the same protein that is required for yeast replication, the first chimeric gene containing a promoter responsive to growth medium conditions and the second chimeric gene containing a promoter operable in mother cells but not daughter cells. This aspect of the invention also contemplates expression vectors and host cells that contain the DNA construct, as well as kits containing such host cells.

A third aspect of the present invention relates to a kit that includes: a first container that contains a first growth medium and yeast cells in the growth medium, the yeast cells possessing two chimeric genes both encoding substantially the same protein that is required for replication, one chimeric gene containing a promoter responsive to growth medium conditions and the other chimeric gene containing a promoter operable in mother cells but not daughter cells, wherein the first growth medium induces expression of the chimeric gene under control of the promoter responsive to growth medium conditions; a second container that contains a growth medium that strongly represses expression of the one chimeric gene comprising the promoter responsive to growth medium conditions; and empty containers for growing yeast cells obtained from the first container in the growth medium of the second container.

A fourth aspect of the present invention relates to a method of identifying quantitative trait loci for aging-related genes in yeast. This method is carried out by providing first and second yeast strains having different replicative lifespans, each strain containing two chimeric genes both encoding substantially the same protein that is required for replication, one chimeric gene containing a promoter responsive to growth medium conditions and the other chimeric gene containing a promoter operable in mother cells but not daughter cells; mating the first and second yeast strains to produce diploid cells; inducing meiosis in the diploid cells to produce spores; isolating and germinating the spores to produce haploid offspring; culturing the haploid offspring under conditions whereby mother cells can replicate and daughter cells cannot; determining the replicable lifespan of haploid offspring; and identifying one or more quantitative trait loci associated with the replicable lifespan of the haploid offspring.

Because of the conservation of many yeast and human pathways implicated in aging and senescence processes, i.e., both signaling and effector pathways, the present invention affords a useful tool for identifying and evaluating the conserved genes involved in those aging and senescence pathways as well as evaluating pharmaceutical agents that can modify such pathways. Furthermore, approximately 20-30% of yeast genes are homologous to human genes. Many more function in analogous processes that are conserved. The possible role of most of these genes in lifespan has not been explored. The present invention promises to speed lifespan analyses by orders of magnitude, particularly when optimized for automated screening of an entire yeast deletion library for genes that both increase and decrease yeast lifespan, and also for chemical screens for compounds that affect lifespan.

DETAILED DESCRIPTION OF THE INVENTION

Figure 1:
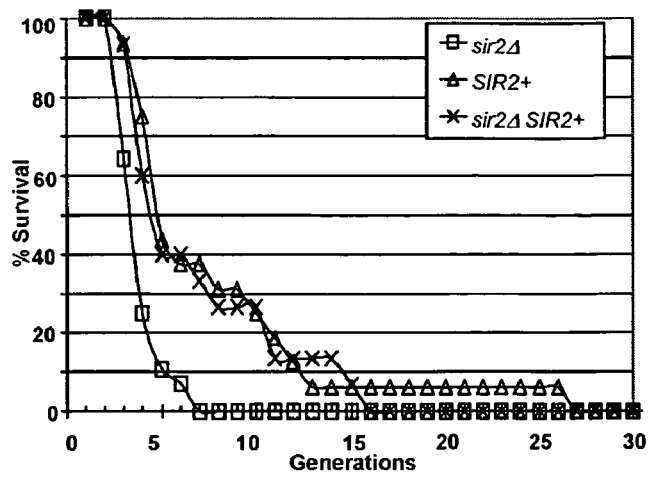
FIG. 1 is a graph illustrating the role of SIR2 for normal replicative lifespan. The parental K6001 strain (SIR2+) has a mean lifespan that is significantly longer than the strain lacking a SIR2 gene (sir2Δ). The expression of SIR2 from a galactose inducible promoter on a plasmid rescues the sir2Δ defect (sir2ΔSIR2+).

The present invention relates to methods of identifying environmental stimuli and/or genes that alters the lifespan of organisms. The organisms preferably are yeast, such as the ascomycetous yeast *Candida, Schizosaccharomyces*, or *Saccharomyces*. Of these, *Saccharomyces cerevisiae* is preferred. It should be appreciated, however, that other yeasts can also be used. Moreover, to the extent that the present invention allows for identification of yeast genes implicated in aging and senescence processes, such genes can be used to identify homologs in mammalian genomes, particularly the human genome, whose function has not been previously identified. Due to the highly conserved nature of these fundamental processes, there is a high correlation between the structure and function of yeast and mammalian (human) homologs. The present invention should greatly speed the future analysis of genes, their mutants, and their chemical activators and antagonists, whose role in aging and lifespan is already known.

The yeast cell cultures that are used in the present invention are asynchronously growing and thus contain a mixture of mother, daughter, and mother-daughter diploids. The yeast cells contain two or more transgenes, preferably though not exclusively in the form of a single genetic cassette, that allow parent yeast cells to grow and replicate on a selective growth medium while daughter yeast cells cannot. The cassette, because of its ability to cause death of daughter cells, is identified herein as a 'DEAD cassette'. The transgenes themselves are chimeric genes and either referred to as such or as DEAD transgenes.

When diploid yeast cells are utilized, both copies of the diploid chromosomes contain the DEAD transgenes. When haploid yeast cells are utilized, only one copy of each DEAD transgene is present.

The DEAD cassette is a DNA construct (maintained either extrachromosomally on a plasmid or integrated directly into the chromosomes) which contains two genes that both encode an essential protein, i.e., one that is required for growth and replication. As discussed in greater detail hereinafter, the essential protein can be a native protein or a foreign protein. The two genes can encode either substantially the same protein or exactly the same protein. By "substantially the same", it is intended that the proteins can be evolutionarily homologous or functionally similar, and may include variations and mutations of the genes encoding these proteins. Functionally similar proteins are those that are at least partially redundant; that is, a homologous protein that can rescue a deletion mutant. Each of the two genes contains, operably linked in the 5' to 3' direction, a yeast-recognized transcription and translation initiation (i.e., promoter) region, a nucleotide coding sequence (i.e., open reading frame) for the essential protein, and a yeast-recognized transcription and translation termination region. By "operably linked" it is intended that expression of the essential protein(s) is under the regulatory control of the promoter and termination regions.

By "yeast-recognized transcription and translation initiation and termination regions" it is intended that the regulatory regions that flank a coding sequence, in this case the nucleotide sequence encoding the essential protein (i.e. the "structural gene" or open reading frame), control transcription and translation of the coding sequence in a yeast. These regulatory regions must be functional in the yeast host. The promoter region provides a binding site for RNA polymerase to initiate downstream (3') transcription of the coding sequence. The transcription termination regulatory sequence may be native to the gene, or may be derived from another source, providing that it is recognized by the yeast host.

The two chimeric genes are different in that their transcription is directed by different promoters. One copy is driven by an inducible promoter that is responsive to growth medium conditions, such as a GAL promoter that is induced to express the essential protein only when the yeast are cultured on a galactose-containing medium, and strongly shut-off or repressed in an alternate condition, such as in the presence of glucose. The other copy is driven by a promoter operable only in mother cells), such as an HO endonuclease promoter. When cultured on a replication-permissive growth medium, both mother and daughter cells can express the essential protein and both can grow and replicate (i.e., logarithmic growth is achieved); yet when cultured on a replication-limited growth medium, only mother cells can express the essential protein and only they can grow and replicate (i.e., only linear growth is achieved).

The nucleotide sequences for the various GAL promoters (e.g., those from GAL1-GAL10) are well known in the art. Of these, the GAL1, GAL7, and GAL10 promoters are preferred because of their tight regulation. The nucleotide sequence of two such promoters, the GAL1/10 bi-directional promoters (SEQ ID NO: 1), is illustrated below:

```
ttatattgaa ttttcaaaaa ttcttacttt tttttggat ggacgcaaag aagtttaata   60
atcatattac atggcattac caccatatac atatccatat ctaatcttac ttatatgttg  120
tggaaatgta aagagcccca ttatcttagc ctaaaaaaac cttctctttg gaactttcag  180
taatacgctt aactgctcat tgctatattg aagtacggat tagaagccgc cgagcgggcg  240
acagccctcc gacggaagac tctcctccgt gcgtcctcgt cttcaccggt cgcgttcctg  300
aaacgcagat gtgcctcgcg ccgcactgct ccgaacaata aagattctac aatactagct  360
tttatggtta tgaagaggaa aaattggcag taacctggcc ccacaaacct tcaaattaac  420
```

```
gaatcaaatt aacaaccata ggatgataat gcgattagtt ttttagcctt atttctgggg    480
taattaatca gcgaagcgat gattttttgat ctattaacag atatataaat ggaaaagctg   540
cataaccact ttaactaata ctttcaacat tttcagtttg tattacttct tattcaaatg    600
tcataaaagt atcaacaaaa aattgtta                                        628
```

Promoter-effective fragments of the above-identified promoter can also be used.

The nucleotide sequence for HO endonuclease promoters are well known in the art, having been reported by Genbank Accession X06979; Stillman et al., "Characterization of a Transcription Factor Involved in Mother Cell Specific Transcription of the Yeast HO gene," *EMBO J.* 7(2):485-494 (1988); Russell et al., "Structure of the *Saccharomyces cerevisiae* HO Gene and Analysis of its Upstream Regulatory Region," *Mol. Cell. Biol.* 6(12): 4281-4294 (1986), each of which is hereby incorporated by reference in its entirety. One exemplary form of the *S. cerevisiae* HO promoter is provided as SEQ ID NO: 2 below:

The termination regions of the two chimeric genes can be the same or different. Any suitably efficient yeast-recognized termination sequence can be employed in the chimeric gene of the present invention. One suitable terminal region is the native α-factor transcription termination sequence as described in U.S. Pat. No. 4,870,008 to Brake, which is hereby incorporated by reference in its entirety. Another suitable terminal region is the native cytochrome c transcription termination sequence (Genbank Accession M34014; Butler et al., "RNA Processing Generates the Mature 3' End of Yeast CYC1 Messenger RNA in vitro," *Science* 242(4883):1270-1274 (1988); Guo et al., "Signals Sufficient for 3'-end Formation of Yeast mRNA," *Mol. Cell Biol.* 16(6):2772-2776

```
gttaaaagtt acatcctttt tttcattttt ccctacgctc agggcactgt actgcccgtg    60
cctgcgatga gatacatcaa tttaaaaaaa aaaccagcat gctataatgc tggagcaaaa   120
atttcaatca gaaatagaaa agacctcaac agtaattaac ccaaaggggt atcaaataat   180
cgatgtgctt tttcactcta cgaatgatct gtgagaaact gatttgggcc gaatcgcgta   240
aaaagtttga ttcgtggcgg ctaatgtctg aggggctcca acaggctcgt agagcctcgt   300
ttcttgaggg cacaaaatgt ccaggtaata ttcccaagaa agaaccgcag agtgctttga   360
taaatcggtt acaggtctta acgtaggttt tgtctcgcta attgctattg agtaagttcg   420
atccgtttgg cgtcttttgg ggtgtaacgc caaacttatt acttttccta tttgaggttg   480
gtattgattg ttgtcaaaga atgaaaatat acacaaacgc cacaatatac gtaccaggtt   540
cacgaaaact gatcgtatgg ttcatacccct gacttggcaa acctaatgtg accgtcgctg   600
attagcggat cacgaaaagt gatctcgata caattagagg atccacgaaa atgatgtgaa   660
tgaatacatg aaagattcat gagatctgac aacatggtag acgtgtgtgt ctcatggaaa   720
ttgatgcagt tgaagacatg tgcgtcacga aaaagaaat caatcctaca cagggcttaa    780
gggcaaatgt attcatgtgt gtcacgaaaa gtgatgtaac taaatacacg attaccatgg   840
aaattaacgt acctttttttg tgcgtgtatt gaaatattat gacatattac agaaagggtt   900
cgcaagtcct gtttctatgc cttctctta gtaattcacg aaataaacct atggtttacg    960
aaatgatcca cgaaaatcat gttattattt acatcaacat atcgcgaaaa ttcatgtcat  1020
gtccacatta acatcattgc agagcaacaa ttcattttca tagagaaatt tgctactatc  1080
acccactagt actaccattg gtacctacta ctttgaattg tactaccgct gggcgttatt  1140
aggtgtgaaa ccacgaaaag ttcaccataa cttcgaataa agtcgcggaa aaaagtaaac  1200
agctattgct actcaaatga ggtttgcaga agcttgttga agcatgatga agcgttctaa  1260
acgcactatt catcattaaa tatttaaagc tcataaaatt gtattcaatt cctattctaa  1320 atggcttta tttctattac aactattagc tctaaatcca tatcctcata agcagcaatc  1380
aattctatct atactttaaa                                               1400
```

Promoter-effective fragments of the above-identified HO promoter can also be used.

(1996); Guo et al., "3'-end-forming Signals of Yeast mRNA," *Mol. Cell Biol.* 15(11):5983-5990 (1995), each of which is hereby incorporated by reference in its entirety). An exemplary cytochrome c transcription termination sequence is provided as SEQ ID NO: 3 below:

```
agatccgctc taaccgaaaa ggaaggagtt agacaacctg aagtctaggt ccctatttat    60
ttttttatag ttatgttagt attaagaacg ttatttatat ttcaaatttt tctttttttt   120
ctgtacagac gcgtgtacgc atgtaacatt atactgaaaa ccttgcttga gaaggtttt    179
```

The essential protein that is required for replication can be any yeast protein which, when knocked-out, degraded, or otherwise inhibited, results in death (and preferably within one cycle). A large number of such proteins have been identified by deletion projects of yeast genomes, as reported on the *Saccharomyces* Genome Database (currently hosted by Stanford University), and the *Schizosaccharomyces* Genome Database (currently hosted by the Sanger Institute). Essential proteins fall into any number of classes, including without limitation DNA polymerases, cell cycle proteins (i.e., clock proteins, checkpoint control proteins, morphogenetic proteins), etc.

The particular essential protein selected for expression by the two chimeric genes of the DEAD cassette can be native proteins that are specific for the species of yeast employed. Thus, *Saccharomyces cerevisiae* cell cycle proteins are a preferred native protein when the methods of the present invention utilize *Saccharomyces cerevisiae*, *S. pombe* cell cycle proteins are a preferred native protein when the methods of the present invention utilize *S. pombe*, etc.

Exemplary *Saccharomyces cerevisiae* cell cycle proteins that can be used in accordance with the present invention include, without limitation, CDC2 (Genbank Accessions X15477 and NC_001136, each of which is hereby incorporated by reference in its entirety), CDC3 (Genbank Accessions L16548 and NC_001144, each of which is hereby incorporated by reference in its entirety), CDC4 (Genbank Accessions X05625 and NC_001138, each of which is hereby incorporated by reference in its entirety), CDC6 (Genbank Accessions X65299, M22858, J04734, and NC_001142, each of which is hereby incorporated by reference in its entirety), CDC7 (Genbank Accessions M12624 and NC_001136, each of which is hereby incorporated by reference in its entirety), CDC8 (Genbank Accessions K02116, K01738, and NC_001142, each of which is hereby incorporated by reference in its entirety), CDC9 (Genbank Accessions X03246 and NC_001136, each of which is hereby incorporated by reference in its entirety), CDC10 (Genbank Accessions L16549 and NC_001135, each of which is hereby incorporated by reference in its entirety), CDC13 (Genbank Accessions M76550 and NC_001136, each of which is hereby incorporated by reference in its entirety), CDC16 (Genbank Accessions X06165 and NC_001143, each of which is hereby incorporated by reference in its entirety), CDC20 (Genbank Accessions X59428 and NC_001139, each of which is hereby incorporated by reference in its entirety), CDC23 (Genbank Accessions D00610 and NC_001140, each of which is hereby incorporated by reference in its entirety), CDC24 (Genbank Accession NC_001133, which is hereby incorporated by reference in its entirety), CDC26 (Genbank Accession NC_001138, which is hereby incorporated by reference in its entirety), CDC27 (Genbank Accession NC_001134, which is hereby incorporated by reference in its entirety), CDC28 (Genbank Accession X80224 and NC_001134, each of which is hereby incorporated by reference in its entirety), CDC34 (Genbank Accessions M21877 and NC_001136, each of which is hereby incorporated by reference in its entirety), CDC42 (Genbank Accessions X51906 and NC_001144, each of which is hereby incorporated by reference in its entirety), and CDC53 (Genbank Accessions U43564 and NC_001136, each of which is hereby incorporated by reference in its entirety). Other cell cycle proteins now known or hereafter identified can likewise be used in practicing the present invention.

Homologs of the above-identified *Saccharomyces cerevisiae* cell cycle proteins have been identified in other yeasts (including *Saccharomyces sensu* species, *Candida*, and *Schizosaccharomyces*) and can likewise be employed when practicing the present invention using those alternative hosts. Further cell cycle proteins that are present in other yeast genomes but lacking a homolog in the *Saccharomyces cerevisiae* can likewise be utilized in accordance with the present invention.

The essential protein can also be recombinantly modified to incorporate a degradation motif, such as a PEST motif, into its amino acid sequence, thereby facilitating more rapid degradation of the protein following its expression.

As an alternative to essential native proteins, non-native proteins that are essential for the normal replication of yeast can also be used. Such proteins are responsible for essential gain-of-function activities, such as antibiotic resistance. By way of example, the KAN (kanamycin resistance) gene can be used, expressed under control of the HO promoter only in mother cells and under control of a GAL promoter in both mother and daughter cells cultured in a galactose-containing growth media (see Guldener et al., "A New Efficient Gene Disruption Cassette for Repeated Use in Budding Yeast," *Nucleic Acids Res.* 24:2519-2524 (1996), which is hereby incorporated by reference in its entirety). It may be desirable to modify the KAN gene, for example, by incorporating a PEST degradation sequence to shorten the protein's half-life, so that daughter cells do not inherit sufficient protein to survive for some generations. Any similar gene or mutation that causes resistance to an antibiotic or other chemical or environmental condition may be used in the present invention.

Regardless of whether the protein to be expressed in a native protein or a non-native protein, the chimeric DEAD transgenes, and the DEAD cassettes containing those genes, can be constructed using well known molecular biological techniques, allowing for ligation of previously identified nucleotide sequences into a single construct or vector, or integrated into the chromosome(s) with nucleotide-to-nucleotide specificity as desired. Such techniques are disclosed, for example, in Sambrook et al., *Molecular Cloning: A Laboratory Manual*, Second Edition, Cold Spring Harbor Press, NY (1989), which is hereby incorporated by reference in its entirety.

According to one approach, each chimeric gene can be prepared by simply inserting the coding sequence of the essential protein into a previously designed empty expression vector that contains restriction enzyme cleavage sites appropriately positioned for opening of the vector between the 5' and 3' regulatory regions. Thus, upon insertion of the coding sequence into such an empty expression vector, the chimeric gene is prepared simultaneously.

According to an alternative approach, each chimeric gene can be assembled first and then inserted into an appropriate expression vector using appropriately positioned restriction enzyme cleavage sites.

Most expression vectors used for yeast studies are shuttle vectors, which contain sequences permitting them to be selected and propagated in *E. coli*, thus allowing for convenient amplification and subsequent alteration in vitro. The most common yeast vectors originated from pBR322 and contain an origin of replication (ori), promoting high copy-number maintenance in *E. coli*, and one or more selectable antibiotic markers (e.g., $Amp^R$ and $Tet^R$, which confer resistance to ampicillin and tetracycline, respectively).

In addition, all yeast vectors contain markers that allow selection of transformants containing the desired plasmid. The most commonly used yeast markers include URA3, HIS3, LEU2, TRP1 and LYS2, which complement specific auxotrophic mutations in yeast, such as ura3-52, his3-Δ1, leu2-Δ1, trp1-Δ1 and lys2-201. These complementable yeast mutations have been chosen because of their low-reversion rate. Also, the URA3, HIS3, LEU2 and TRP1 yeast markers can complement specific *E. coli* auxotrophic mutations. The URA3 and LYS2 yeast genes have an additional advantage because both positive and negative selections are possible.

Although there are numerous kinds of yeast shuttle vectors, those used currently can be broadly classified as either integrative vectors, YIp; autonomously replicating high copy-number vectors, YEp; or autonomously replicating low copy-number vectors, YCp. As an alternative, yeast artificial chromosomes, YACs, can also be employed.

The YIp integrative vectors do not replicate autonomously, but integrate into the genome at low frequencies by homologous recombination. Integration of circular plasmid DNA by homologous recombination leads to a copy of the vector sequence flanked by two direct copies of the yeast sequence. The site of integration can be targeted by cutting the yeast segment in the YIp plasmid with a restriction endonuclease and transforming the yeast strain with the linearized plasmid. The linear ends are recombinogenic and direct integration to the site in the genome that is homologous to these ends. In addition, linearization increases the efficiency of integrative transformation from 10- to 50-fold. The YIp vectors typically integrate as a single copy. YIp plasmids with two yeast segments, such as YFG1 and URA3 markers, have the potential to integrate at either of the genomic loci, whereas vectors containing repetitive DNA sequences, such as Ty elements or rDNA, can integrate at any of the multiple sites within genome. Strains transformed with YIp plasmids are extremely stable, even in the absence of selective pressure. However, plasmid loss can occur at approximately $10^{-3}$ to $10^{-4}$ frequencies by homologous recombination between tandemly repeated DNA.

When integration is desired, the DEAD cassette can be inserted into the yeast genome such that the native essential gene is disrupted, and effectively replaced by the DEAD transgenes.

The YCp yeast centromere plasmid vectors are autonomously replicating vectors containing centromere sequences, CEN, and autonomously replicating sequences, ARS. The YCp vectors are typically present at very low copy numbers, from 1 to 3 per cell but possibly more, and are lost in approximately $10^{-2}$ cells per generation without selective pressure. In many instances, the YCp vectors mimic the behavior of chromosomes during meiosis, as well as during mitosis. The ARS sequences are believed to correspond to the natural replication origins of yeast chromosomes, and all of them contain a specific consensus sequence. ARS1, which is in close proximity to TRP1, is the most commonly used ARS element for YCp vectors, although others have been used. The CEN function is dependent on three conserved domains, all of which are required for mitotic stabilization of YCp vectors. CEN3, CEN4, and CEN11 are commonly used centromeres that can be conveniently manipulated. The stability and low copy-number of YCp vectors make them the ideal choice for cloning vectors, for construction of yeast genomic DNA libraries, and for investigating the function of genes altered in vivo.

When the DEAD cassette is meant to be maintained as an extrachromosomal plasmid, it will be necessary to inactive, usually by deletion, the chromosomal copy of the essential gene employed in the DEAD transgenes. This can be carried out using known techniques.

Once the DEAD cassette has been prepared, it can be transformed into a selected host strain of yeast. The selected host strain of yeast can be a naturally-occurring isolate or a laboratory isolate. Yeast and other microorganisms are generally available from a variety of sources, including the Yeast Genetic Stock Center, Department of Biophysics and Medical Physics, University of California, Berkeley, Calif.; and the American Type Culture Collection, Rockville, Md. To the extent that the genome of a BY strain has been used for the yeast genome project, and its genomic sequence is therefore known, use of BY host strains will facilitate and simplify the transformation of the yeast with a DEAD cassette and/or knockout of a native essential gene (that is being expressed by the DEAD transgenes).

Methods of introducing exogenous DNA into yeast hosts are well known in the art. There is a wide variety of ways to transform yeast. For example, spheroplast transformation is taught by Hinnen et al., "Transformation of Yeast Chimeric ColE1 Plasmid Carrying LEU2," *Proc. Natl. Acad. Sci. USA* 75:1919-1933 (1978); EPO Publication No. 45,573 to Stinchcomb et al., each of which is hereby incorporated by reference in its entirety. Transformants are cultured in an appropriate nutrient medium, and, where appropriate, maintained under selective pressure to insure retention of endogenous DNA.

As an alternative approach, the DNA construct which forms the DEAD cassette can be a product of polymerase chain reaction ("PCR") that is integrated directly into the host yeast genome. This may be desirable to ensure, for example, proper control over gene expression. Methods to replace, alter, or modify in any way the nucleotide sequence of a chromosomally-encoded DNA locus exploit the high fidelity homologous recombination system of *S. cerevisiae*. The introduction by transformation of segments of DNA that share homology at both ends with sequences within the chromosome results in integration with high frequency at the preferred site, although this should be confirmed using PCR as integration can occur elsewhere. Successful integrations are identified by the incorporation of an antibiotic resistance or auxotrophic marker that can be selected for in the growth medium. For example, the CDC6 gene of one strain can be deleted by replacing the gene with a DNA segment amplified by PCR from the homologous region of the chromosome from a strain whose CDC6 gene was previously replaced with a KAN gene. Alternatively, the gene that is targeted to be deleted can be replaced with a sequence of DNA containing the KAN gene flanked by 40-60 nucleotides of DNA that are homologous to the sequences that lie just outside the coding sequence of the CDC6 gene. There are many modifications of these techniques commonly in use. Many applications require the construction of plasmids containing the engineered segments, which are then amplified using PCR and transformed into the host strain.

PCR-mediated gene disruption requires prior knowledge of the DNA sequence for the gene of interest. (Many yeast databases are now available and others are being assembled and reported for future use.) This knowledge allows the precise gene deletion, or precise insertion of DNA sequence, directly into the genome without having to first clone the gene onto a plasmid. The procedures have been employed with success in yeast. See, e.g., Lorenz et al., "Gene Disruption with PCR Products in *Saccharomyces cerevisiae,*" *Gene* 158: 113-117 (1995); Brachmann et al., "Designer Deletion Strains Derived from *Saccharomyces cerevisiae* S288C: A Useful Set of Strains and Plasmids for PCR-mediated Gene Disruption and Other Applications," *Yeast* 14:115-132 (1998), each of which is hereby incorporated by reference in its entirety.

One yeast strain that can be used in the assays of the present invention is *S. cerevisiae* strain K6001, which carries two distinct non-native genes (i.e., not contained within a single cassette). This strain was originally developed for the study of mating-type switching (Bobola et al. "Asymmetric Accumulation of Ash1p in Postanaphase Nuclei Depends on a Myosin and Restricts Yeast Mating-Type Switching to Mother Cells," *Cell* 84:699-709 (1996), which is hereby incorporated by reference in its entirety). K6001 cells contain two independent copies of CDC6 expressed from either the repressible GAL1or mother-cell specific HO promoters. Cdc6p is an essential protein required for DNA replication. Transcription from the HO promoter in daughter cells is prevented by Ash1p, which is expressed exclusively in daughter cells (Sil, et al., "Identification of Asymmetrically Localized Determinant, Ash1p, Required for Lineage-Specific Transcription of the Yeast HO Gene," *Cell* 84:711-22 (1996), which is hereby incorporated by reference in its entirety). When K6001 cells are cultured on galactose, GAL1::CDC6 is expressed in both mother and daughter cells, sustaining the replication of both. However, when the GAL1::CDC6 gene is repressed by glucose, only the mother-specific expression of HO::CDC6 remains to support growth. Given the tight regulation of the GAL1promoter, DNA replication fails and daughter cells arrest after one, or at most a few ectopic cytokineses. As a result, K6001 cultures grow approximately linearly in glucose (daughter cells accumulate and contribute to the optical density of the culture) until the mother cells reach their replicative capacity and cease producing daughter cells. Since Cdc6 is naturally unstable, and the GAL1 promoter is efficiently shut off in glucose, the transition from log growth to linear growth is relatively tight and rapid.

As identified above, DEAD cassettes that utilize cell cycle proteins other than CDC6, or other essential proteins whose depletion or lack of expression results in rapid cell death, are contemplated.

The assay for replicative lifespan in accordance with the present invention is preferably carried out in parallel using a control strain that is cultured under identical conditions with the exception of a single genetic or environmental variable, or a combination thereof, that is tested for its affect on replicative lifespan. Thus, both a control cell culture and one or more test cell cultures is provided. The control cell cultures and the one or more test cell cultures are cultured under conditions whereby mother yeast cells can replicate and daughter yeast cells cannot. For example, when using DEAD cassettes that employ the HO promoter for one chimeric gene and a GAL promoter for the other chimeric gene, culturing of the control and test cultures in a glucose-containing media represses expression of the essential gene that is under control of the GAL promoter. In such a case, the daughter cells are unable to express the essential protein and consequently die, whereas mother cells are able to express the essential protein (due to their HO-induced expression) and consequently continue to grow and replicate until they reach senescence. By assessing the replicative lifespan of the control cell culture and the one or more test cell cultures, it is possible to make a determination as to whether the mother cells in the one or more test cell cultures exhibit a change in replicable lifespan relative to the mother cells in the control cell culture. An increase in the replicable lifespan for mother cells of a test cell culture indicates that the genotype modification, the environmental stimulus, or the combination thereof enhances the replicable lifespan of the mother cells in the test cell culture. Likewise, a decrease in the replicable lifespan for mother cells of a test cell culture indicates that the genotype modification, the environmental stimulus, or the combination thereof diminishes the replicable lifespan of the parent yeast cells in the test cell culture.

In accordance with one embodiment of the present invention, a host strain of yeast carrying the DEAD cassette is characterized by the presence of a genotype modification involving either a nonessential gene or an essential gene, in which case the genotype modification is non-lethal. Based on current knowledge of the *Saccharomyces cerevisiae* genome, it is believed that the genome contains approximately 4800 open reading frames encoding non-essential genes, many of which remain uncharacterized. An entire library of single- and multiple-mutants can be screened using the present invention to identify those nonessential genes that affect replicative lifespan. The genotype modification to the nonessential gene can be a deletion mutant, an overexpression mutant, an addition mutant, or a mutant encoding a variant protein. The genotype modification to the essential gene can be an overexpression mutant, a reduced expression mutant, or a mutant encoding a functional variant protein.

In a variation of this embodiment, the host strain of yeast to be screened can be a humanized yeast. That is, a yeast gene that regulates replicative lifespan is replaced with a human homolog of the yeast gene or DNA sequence (see Henning et al., "Humanizing the Yeast Telomerase Template," *Proc. Natl. Acad. Sci. USA* 95:5667-5671 (1998), which is hereby incorporated by reference in its entirety). The human homolog can be associated with a particular disease state in humans or it could simply be an orphan receptor (Wilson et al., "Orphan G-protein-coupled Receptors: The Next Generation of Drug Targets?" *Br. J. Pharmacol.* 125(7):1387-1392 (1998), which is hereby incorporated by reference in its entirety). Exemplary human homologs include, without limitation, ras, bax (Priault et al., "Yeast as a Tool to Study Bax/Mitochondrial Interactions in Cell Death," *FEMS Yeast Res.* 4(1):15-27 (2003), which is hereby incorporated by reference in its entirety), sir2, sgs1 which is homologous to the human Werner syndrome gene (wrn) and has previously been demonstrated to be rescued by transformation with the human Blooms syndrome (BS) gene (Heo et al., "Bloom's Syndrome Gene Suppresses Premature Aging Caused by Sgs1 Deficiency in Yeast," *Genes Cells* 4:619-625 (1999), which is hereby incorporated by reference in its entirety). Other homologs have been and will continue to be identified (see Steinmetz et al., "Systematic Screen for Human Disease Genes in Yeast," *Nat. Genet.* 31(4):400-404 (2002), which is hereby incorporated by reference in its entirety). Where the particular human homolog is associated with a particular disease state, the methods of the present invention can be used to identify agents, such as pharmaceutical agents, that can be used to overcome or diminish the effects of the disease state, as evidenced by an increase in replicative lifespan when the humanized yeast is cultured in the presence of such agents.

The affects of non-yeast genes which do not have yeast homologs, but exert an influence on the physiology of the yeast cell, may also be investigated for effects on replicative lifespan. For example, human bax is able to induce cell death in yeast by a mechanism analogous to its action in human cells, even though *S. cerevisiae* lacks a functional or structural homolog of bax (Camougrand et al., "The Product of the UTH1 Gene, Required for Bax-Induced Cell Death in Yeast, Is Involved in the Response to Rapamycin," *Mol. Microbiol.* 47:495-506 (2003), which is hereby incorporated by reference in its entirety).

In accordance with another embodiment of the present invention, a host strain of yeast carrying the DEAD cassette can be exposed to an environmental stimulus (other than a pro-oxidant, which is known to negatively affect lifespan) to assess whether the environmental stimulus increases or decreases replicative lifespan. The environmental stimulus can be a chemical agent, a mixture of natural or synthetic organic or inorganic products, plant or animal extracts, or tinctures, as well as combinations thereof.

In accordance with another embodiment of the present invention, a homozygous diploid host strain of yeast carrying two identical copies of the DEAD cassette (homozygous for the DEAD cassette) but having a mutation in one copy of any single or multiple gene(s) (heterozygous for specified essential genes) can be assayed for affects on lifespan. This embodiment provides a method to investigate the influence of essential genes on lifespan, since a reduced copy number of essential genes can reduce the function of the gene without resulting in cell death or loss of growth and division (see Giaever et al., "Chemogenomic Profiling: Identifying the Functional Interactions of Small Molecules in Yeast," *Proc. Natl. Acad Sci. USA* 101:793-798 (2004), which is hereby incorporated by reference in its entirety).

In accordance with another embodiment of the present invention, a host strain of yeast carrying a DEAD cassette can also overexpress a gene carried on a high copy number plasmid (ARS) such that overexpression of the gene may increase or decrease replicative lifespan. The overexpressed genes may be either nonessential or essential, and may also derive from species other than *Saccharomyces cerevisiae* if properly expressed using appropriate expression systems.

In accordance with another embodiment of the present invention, a host strains of yeast carrying the DEAD cassette also possesses a genotype modification that is known to affect replicative lifespan (i.e., one that has previously been identified, perhaps using the present invention), and this host strain is exposed to an environmental stimulus to assess whether the environmental stimulus increases or decreases replicative lifespan. In this embodiment, the genotype modification can either increase or decrease replicative lifespan, and as noted above the genotype modification can involve a human gene. The environmental stimulus can be any chemical agent, a mixture of natural or synthetic organic or inorganic products, plant or animal extracts or tinctures, or combinations thereof. This embodiment can be used to assess whether the environmental stimulus can overcome or diminish a decreased replicative lifespan phenotype caused by the genotype modification, or assess whether the environmental stimulus effects an increased replicative lifespan phenotype.

The assay for replicative lifespan can be carried out in both liquid and solid growth media. Based on the form of media, different detection procedures can be employed to determine the replicative lifespan of control and test cell cultures.

When employing liquid growth media, the cultures can be grown in any suitable container (e.g., cuvettes or microtiter plate wells) that allow for growth curve analysis based on the optical density of the culture or other method that allows quantification of cell number as a function of time. Thus, growth curve analyses are performed on both the control cell culture and the one or more test cell cultures, and then an assessment is made as to whether or not a difference exists between the growth curves of the control cell culture and the one or more test cell cultures.

The growth curve analysis is particularly suitable for large-scale automation for purposes of screening either large numbers of genetic variations, environmental variations, or combinations thereof. Warringer et al. ("Automated Screening in Environmental Arrays Allows Analysis of Quantitative Phenotypic Profiles in *Saccharomyces cerevisiae*," *Yeast* 20:53-67 (2003), which is hereby incorporated by reference in its entirety) recently developed a methodology for large-scale automated growth curve analysis of yeast in microtiter plate wells. Their study on microcultivation describes suitable software and hardware, and includes a comparison of the physiology of cells grown in plastic microtiter plates versus glass E-flasks. Methods are described that allow detailed and reproducible growth curve measurements from early log phase to stationary phase.

When employing a solid phase growth media, the culture can be grown in any suitable container (e.g., plates) that allow for manual or optical analysis based on colony size. Individual mother cells are placed onto the growth media to begin the assay, resulting in the formation of a microcolony that represents the mother cell and the daughter cells that form (but eventually die). The longer the lifespan of the mother cell (i.e., the greater replication events that occur prior to senescence), the larger the colony size will be.

The traditional approach for assessing replicative lifespan involves identifying and removing by manual dissection the daughter cells that arise from the mother cells. This traditional approach is costly, time-consuming, and subject to human error. While less desirable, this traditional approach can be employed in the present invention, although the daughter cells do not have to be manually removed following each replicative cycle since they are themselves defective in replication. Thus the total number of cells in a colony of cells can be manually counted after a period of time passes that is sufficient for all the mother cells to stop dividing and senesce.

Alternatively, a preferred approach utilizes an optical assessment of colony size. Basically, a digital image of the microcolonies is captured for both the control and test cultures, and then the two-dimensional area, or appropriate morphometric parameter, of colonies in each of the images is calculated, where the two-dimensional area of or the morphometric parameter for a colony equates to the replicable lifespan of the mother cell. Hence, the larger the two-dimensional area of the colony, the higher the replicative lifespan. The image capture can be obtained using conventional microscopy and digital camera equipment, although modifications may increase the efficiency, reproducibility, quality of image, and speed of the process. The image can be analyzed using software programs currently widely used by astronomers for the efficient and accurate measurement of compact objects under crowded conditions (with densities and scales much larger than those encountered in these yeast screening assays). Exemplary astronomical crowded-field algorithms that can be used in the present invention include, without limitation: DAOPHOT (Stetson, "DAOPHOT: A Computer Program for Crowded-field Stellar Photometry," *Pub. Astron. Soc. Pac.* 99:191-222 (1987), which is hereby incorporated by reference in its entirety), XStarfinder (Diolaiti et al., *Proc. SPIE* 4007:879 (2000), which is hereby incorporated by reference in its entirety) which is very similar to DAOPHOT, and the CLEAN algorithm (e.g., Clark, "An Efficient Implementation of the Algorithm 'CLEAN'," *Astron. Astrophys.* 89:377-378 (1980), which is hereby incorporated by reference in its entirety). All of these routines are freely available in many programming languages, including IDL (Research Systems Inc.) which is preferred. The image file format can be adapted, e.g., to IDL, for the efficient reduction of digital images for yeast-colony assays. This adaptation is expected to produce a substantial reduction in data-processing time, and possibly to produce somewhat more accurately-determined properties of individual colonies (Clark, *Astron. Astrophys.* 89:377 (1980), which is hereby incorporated by reference in its entirety).

It is intended that both the growth curve analysis and the optical assessment of colony size will permit large-scale automation for simultaneous screening of ten or more, preferably one-hundred or more, and most preferably one-thousand or more test cell cultures in parallel with appropriate control cell cultures. It is reasonable to expect that, depending on the number of workers and apparatuses, at least one hundred thousand test cultures can be screened in a period of weeks or months.

Regardless of the approach used to determine the replicative lifespan of the microcolonies, survival data is often fitted to a Gompertz mortality rate equation as described by Wilson, "A Comparison of Methods for Estimating Mortality Parameters from Survival Data," *Mech. Aging Develop.* 66:269-281 (1993), which is hereby incorporated by reference in its entirety. Non-linear regression analysis using a Simplex algorithm to fit the key parameters in the Gompertz Survival function is described (by Wilson) that yields reliable and consistent results. This approach can be adapted to calculate the Gompertz parameters as well as mean lifespan of replicative lifespan as it occurs in the DEAD assay. This algorithm can be used to rapidly fit the survival data from many assays for comparative purposes.

Also contemplated are kits that will facilitate the performance of the screening assays of the present invention. The kits are intended to include one or more of the following: (i) a first container that includes a first growth medium and yeast cells in the growth medium, the yeast cells possessing a DEAD cassette, wherein the first growth medium induces expression of the chimeric gene under control of the promoter responsive to growth medium conditions (i.e., daughter cells can grow and replicate); (ii) a second container that contains a growth medium that strongly represses expression of the one chimeric gene comprising the promoter responsive to growth medium conditions; (iii) empty containers for growing yeast cells obtained from the first container in the growth medium of the second container, preferably in the form of microtiter well plates, although other formats can be utilized; and instructions for culturing the yeast cells in the growth medium of the second container and determining the replicable lifespan of mother cells.

In addition to the above approach for screening, it is also possible to utilize the DEAD cassettes to identify quantitative trait loci ("QTL") for lifespan in yeast. In this fashion it should be possible to identify natural nucleotide variants of a lifespan-affecting gene or genes that has been selected for by natural selection or other evolutionary mechanism to be optimally adaptive to a particular environment or stress condition. Yeast as a model for QTL study of aging has several clear advantages. First, its meiosis generate gametes in encapsulated asci, which enables segregation of genotypes in a single meiosis event to be readily traced. Second, it has high recombination rate which enables fine QTL mapping. Third, yeast has a short lifespan. Fourth, as a powerful genetics model, the vast collection of yeast mutation strains can greatly accelerate the QTL analysis. These advantages of yeast in QTL study is demonstrated by a recent study in which three loci associated with a high-temperature trait are identified (Steinmetz et al., "Dissecting the Architecture of a Quantitative Trait Locus in Yeast," *Nature* 416(6878):326-330 (2002), which is hereby incorporated by reference in its entirety).

The QTL analysis can follow the approach of Steinmetz et al., ("Dissecting the Architecture of a Quantitative Trait Locus in Yeast," *Nature* 416(6878):326-330 (2002), which is hereby incorporated by reference in its entirety), or other QTL analyses identified in the future. Basically, two or more yeast strains having different replicative lifespans (each containing a DEAD cassette or two chimeric genes of the type described above, both encoding substantially the same protein that is required for replication) can be used in the analysis. Strains are mated two at a time to produce diploid cells. Meiosis is induced using standard procedures to produce spores. The spores are then isolated and germinated to produce haploid (F1 hybrid) offspring. The haploid offspring are cultured under the conditions of a replicative lifespan assay, which involves determining whether the haploid offspring exhibit a replicable lifespan that is different from a standard or merely identifying the phenotypic variation along a continuum (from shortest to longest lifespan). The standard can be that of the parental strains. Typically, the haploid offspring that have the best or the worst replicable lifespan can be selected for QTL analysis, although potentially all haploid offspring can be analyzed. The former is known as selective genotyping. The QTL analysis will identify one or more quantitative trait loci associated with the replicable lifespan of the F1 offspring. In the genome scan, each marker is tested statistically to see whether its alleles are randomly distributed between the two phenotypic extremes. A departure from a random segregation will indicate association of that marker with the quantitative trait. As closely linked markers are correlated, regions rather than single markers are usually detected.

In addition to the classical QTL analysis, a reciprocal hemizygosity analysis can be used to resolve the genetic components of lifespan in any chromosomal regions identified by the QTL analysis. The reciprocal hemizygosity analysis can be performed by producing pairs of heterozygous strains from the original parent strains, each member of a pair carrying reciprocal short deletions within the candidate interval identified from the QTL analysis. This approach allows the effect of individual alleles to be observed in an otherwise uniform genetic background. Therefore, due to the heterozygous genetic background, gene-gene interactions are not masked and will be revealed regardless of which allele combination causes the effect. Additionally, potential lethality is avoided as only one copy of the gene is deleted. Each pair of reciprocal hemizygotes can be tested for replicative lifespan using the assay of the present invention.

EXAMPLES

The following examples are provided to illustrate embodiments of the present invention but are by no means intended to limit its scope.

Example 1

Comparing the Lifespans of SIR2 and sir2Δ Cells by DEAD Assay

SIR2 plays a famous role in the lifespan of *S. cerevisiae, C. elegans,* and *D. melanogaster* (Guarente, "Sir2 Links Chromatin Silencing, Metabolism, and Aging," *Genes. Dev.* 14:1021-1026 (2000), which is hereby incorporated by reference in its entirety). Using standard replicative aging assays, mutant sir2Δ cells exhibit an average lifespan approximately half (~10 generations) that of the wildtype SIR2 cells (~20 generations). Interestingly, mean lifespans vary significantly among yeast strains, so the absolute number of replications in any DEAD assay necessarily requires comparison to a control strain. K6001 SIR2 parental and sir2Δ cells grow logarithmically at virtually identical rates in galactose-containing rich medium, indicating that the sir2 mutation does not affect normal growth. In addition, SIR2 and sir2Δ K6001 cells enter stationary phase at the same optical density in both rich (YP-Gal) and synthetic defined (SCGal). Thus, the growth rates of SIR2 and sir2Δ cells are virtually identical in permissive galactose-containing media. The situation is altogether different when expression of the GAL1::CDC6 gene is repressed in glucose. Both SIR2 and sir2Δ K6001 cells initially grow linearly (after a short lag phase) in YPGlu, but sir2Δ cells stop dividing at a significantly lower $OD_{600}$ than SIR2 cells. The DEAD assay successfully reproduces the well-known result that sir2Δ cells senesce and die in fewer generations than SIR2 cells. The actual number of generations was determined by counting the daughter cells produced by individual mother cells plated onto YPGlu. As shown by cell counts in FIG. 1, the mean lifespan of sir2Δ cells (5 daughters/mother) is about half that of SIR2 cells (11 daughters/mother) on YPGlu. The sir2Δ lifespan defect was rescued by expressing SIR2 from a plasmid (FIG. 1). Thus, the DEAD assay reproduces the important role of SIR2 in replicative lifespan in both liquid (by $OD_{600}$) and solid (by cell counts) media.

Example 2

Confirming the Role of Sgs1 as a Lifespan-Regulating Gene, by DEAD Assay

The recQ-like helicase gene SGS1 is required for normal replicative lifespan of *S. cerevisiae* (Heo et al., "Bloom's Syndrome Gene Suppresses Premature Aging Caused by Sgs1 Deficiency in Yeast," *Genes Cells* 4:619-625 (1999), which is hereby incorporated by reference in its entirety). SGS1 is homologous to the human Werner syndrome gene, WRN, which causes a recessive disorder characterized by premature aging, and Bloom syndrome (BS) gene, which causes a recessive disorder characterized by short stature, and immunodeficiency (Watt et al., "SGS1, a Homologue of the Bloom's and Werner's Syndrome Genes, Is Required for Maintenance of Genome Stability in *Saccharomyces cerevisiae,*" *Genetics* 144:935-945 (1996), which is hereby incorporated by reference in its entirety).

Figure 2:
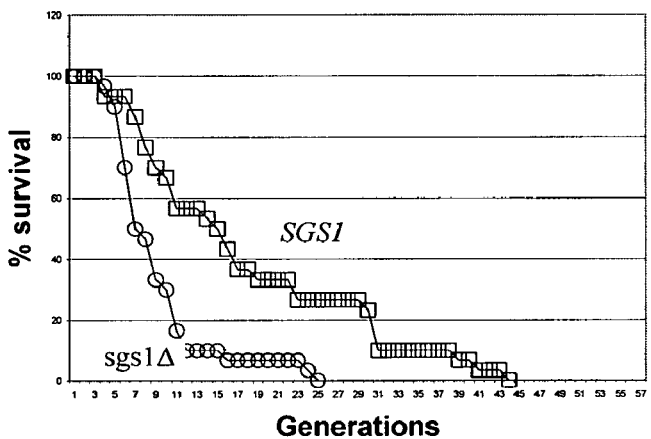
FIG. 2 is a graph illustrating the role of SGS1 for normal replicative lifespan. The parental K6001 strain (SGS1+) has a mean lifespan that is significantly longer than the strain lacking a SGS1 gene (sgs1Δ).

The DEAD assay was used to assess the effect of deleting SGS1 on replicative lifespan. Normal K6001 cells (SGS1+) and K6001 cells containing a complete deletion of the SGS1 coding region (sgs1Δ) were cultured in permissive galactose-containing medium and individual cells were positioned on glucose-containing agar plates. After 48 hrs at 30° C. the number of daughter cells in each microcolony was counted by microdissection and plotted as a survival curve. As shown in FIG. 2, SGS1+ cells had a significantly longer mean lifespan than sgs1Δ cells. These results confirm that deletion of SGS1 also decreases lifespan as previously reported, and further validates the use of the DEAD assay concept to quantify replicative lifespan.

Tong et al. ("Systematic Genetic Analysis with Ordered Arrays of Yeast Deletion Mutants," *Science* 294:2364-2368 (2001); "Global Mapping of the Yeast Genetic Interaction Network," *Science* 303:808-813 (2004), each of which is hereby incorporated by reference in its entirety) performed a synthetic lethal screen and identified a network of genes that interact genetically—directly (e.g. TOP1) or indirectly (e.g. RAD27)—with SGS1. Twenty-one SGS1 interacting genes were identified, eight of which also interacted with RAD27. Rad27p functions during DNA synthesis to remove RNA primers from Okazaki fragments, but is nonessential. Tong et al. identified an additional 25 genes that interact with RAD27. Other screens have identified additional SGS1-interacting genes that were missed by the SGA screen of Tong et al., such as DNA helicase SRS2, which interacts with SGS1 to decrease lifespan and exhibits an independent synthetic effect on growth rate (McVey et al., "The Short Life Span of *Saccharomyces cerevisiae* Sgs1 and Srs2 Mutants is a Composite of Normal Aging Processes and Mitotic Arrest Due to Defective Recombination," *Genetics* 157:1531-42 (2001), which is hereby incorporated by reference in its entirety). Curiously, deleting RAD9 partially corrected the growth defect of sgs1 srs2 cells, but further decreased the lifespan of srs2 or sgs1 cells (McVey et al., "The Short Life Span of *Saccharomyces cerevisiae* Sgs1 and Srs2 Mutants is a Composite of Normal Aging Processes and Mitotic Arrest Due to Defective Recombination," *Genetics* 157:1531-42 (2001), which is hereby incorporated by reference in its entirety). SGS1 was also shown to interact with another RAD gene, RAD16 (Saffi et al., "Importance of the Sgs1 Helicase Activity in DNA Repair of *Saccharomyces cerevisiae,*" *Curr. Genet. Journal* 37(2): 75-78 (2000), which is hereby incorporated by reference in its entirety); however, the affect of rad16 mutants on lifespan was not assessed. Given the number of known interactions between SGS1 and various RAD genes, it is worthwhile to systematically investigate the possible role of other RAD genes in lifespan.

Another SGS1-interacting gene that is absent form the SGA synthetic lethality screen of Tong et al. (2001) is MGS1. MSG1 encodes a DNA-dependent AAA(+) ATPase that interacts with DNA polymerase δ (Branzei et al., "Characterization of the Slow-Growth Phenotype of *S. Cerevisiae* Whip/ mgs1 Sgs1 Double Deletion Mutants" *DNA Repair* 1(8):671- 682 (2002), which is hereby incorporated by reference in its entirety). In this case, as in many of the synthetic interactions identified by SGA, the double mutant is viable but slow growing. Rates of growth per se should not affect DEAD replicative lifespans. As described in Example 1 above, the DEAD estimates of lifespan for both SIR2 and sir2-Δ are unaffected by growth in rich YPG versus minimal SCGlu media.

Example 3

The Sir2 Activator Resveratrol Extends Replicative Lifespan

Figure 3:
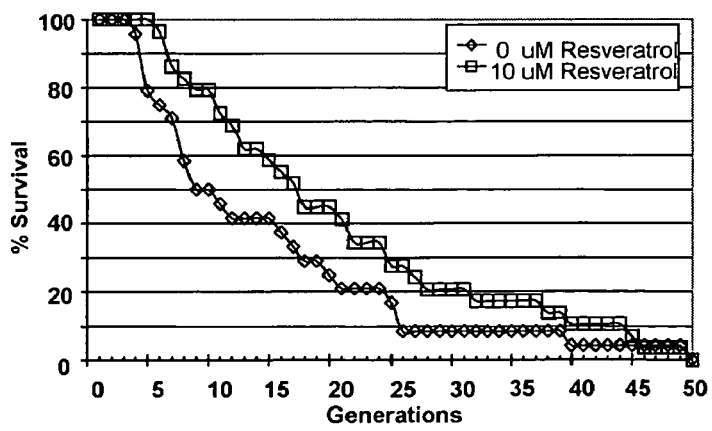
FIG. 3 is a graph illustrating the ability of the Sir2 activator resveratrol to extend replicative lifespan. K6001 cells were cultured in the presence or absence of 10 μM resveratrol. Resveratrol at 10 μM significantly extended the mean lifespan.

Recently it was shown that resveratrol, a natural product found in a variety of plants including grapes (i.e. red wine), actives Sir2 in vitro and extends the replicative lifespan of yeast (Howitz et al., "Small Molecule Activators of Sirtuins Extend *Saccharomyces cerevisiae* Lifespan," *Nature* 425:191-196 (2003), each of which is hereby incorporated by reference in its entirety). As shown in FIG. 3, K6001 cells cultured in 10 μM resveratrol have a longer mean lifespan than those cultured without resveratrol. Therefore, the effect of resveratrol has been replicated using the DEAD assay. This experiment supports the notion that the DEAD assay can be used to screen environmental stimuli, such as those presented by chemical libraries, for those that affect lifespan.

Example 4

The Pro-oxidant Paraquat Reduces Replicative Lifespan

Figure 4:
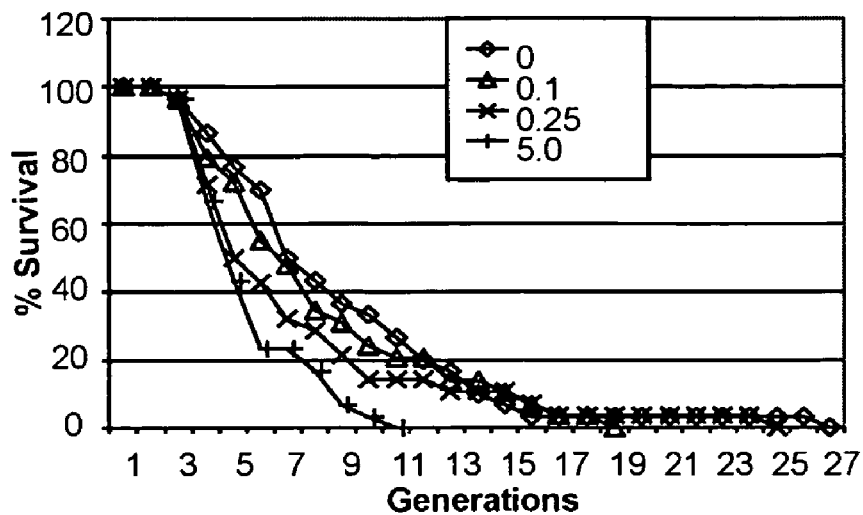
FIG. 4 is a graph illustrating the ability of the pro-oxidant paraquat to decrease replicative lifespan. The mean lifespan of K6001 cells was decreased in a dose-dependent fashion by concentrations of paraquat between 0.1 μM to 5.0 μM.
Figure 5:
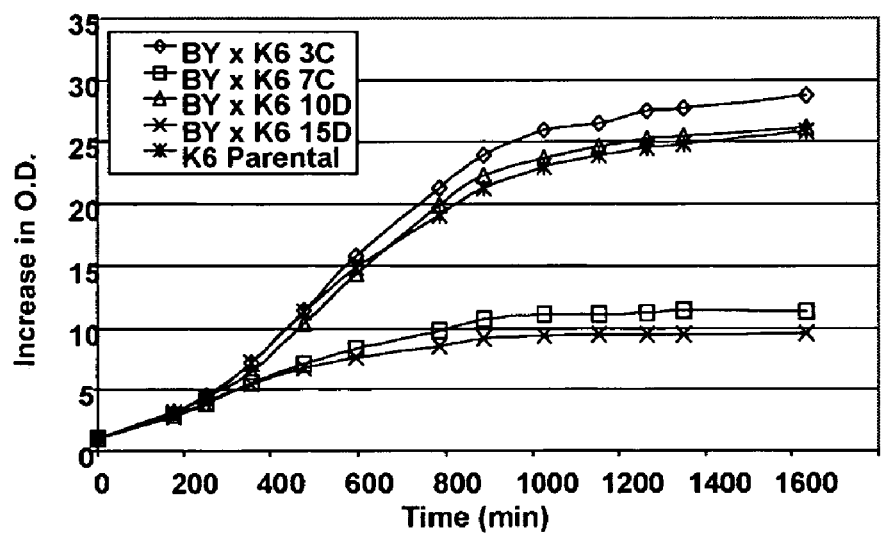
FIG. 5 is a graph illustrating the large biphasic differences in replicative lifespan exhibited by offspring of K6001×BY cells. BY is a common lab strain, derived from S288c, and in which a comprehensive library of nonessential gene deletions is commercially available. K6001 cells, which bear two separate transgenes [GAL1::CDC6 and HO::CDC6], were mated to BY cells. Spores were screened for the presence of the two independently segregating transgenes. The growth of several of these K6001×BY hybrid strains in YPGlu is shown in comparison with the parental K6001 strain.

Pro-oxidants such as paraquat are well-known to reduce replicative lifespan in yeast and to induce apoptosis in mammalian cells (Golden et al., "Oxidative Stress and Aging: Beyond Correlation," *Aging Cell* 1:117-23 (2002); Nestelbacher et al., "The Influence of Oxygen Toxicity on Yeast Mother Cell-specific Aging," *Exp. Gerontol.* 35:63-70 (2000), each of which is hereby incorporated by reference in its entirety). Pro-oxidants have been strongly implicated in a number of model aging systems (Hekimi et al., "Genetics and the Specificity of the Aging Process," *Science* 299:1351-1354 (2003); Johnson et al., "Molecular Biology of Aging," *Cell* 96:291-302 (1999), each of which is hereby incorporated by reference in its entirety). Published reports using the standard assay have not studied paraquat values below 20 µM. As shown in FIG. 4, lifespan of K6001 cells cultured in 5 µM paraquat is apparently shorter than the lifespan of cells cultured in lower concentration. Thus, the effect of paraquat was reproduced using DEAD assay, and more importantly it was demonstrated that, owing to the higher throughput capacity of the DEAD assay versus the standard assay, the DEAD assay may be more suitable for the accurate quantification of replicative lifespan under a variety of genetic and environmental conditions.

Example 5

Variation in Lifespan Among Strains can be Quantified Using the DEAD Assay

The feasibility of using the DEAD assay to rapidly quantify variations in lifespan among the offspring (spores) arising from crosses between two different strains was assessed. QTL analysis of lifespan requires that the replicative lifespans of large numbers of spores be determined. The large numbers involved preclude the use of the standard replicative lifespan assay. As shown in FIG. 4, the DEAD assay allows differences in lifespans of hybrid offspring to be quantified by monitoring $OD_{600}$ in liquid medium. Although these data were collected manually using a spectrophotometer, these data demonstrate the feasibility of high throughput growth analysis of thousands of strains which has been achieved using an automated plate reader (Warringer et al., "Automated Screening in Environmental Arrays Allows Analysis of Quantitative Phenotypic Profiles in *Saccharomyces cerevisiae*," *Yeast* 20:53-67 (2003), which is hereby incorporated by reference in its entirety). The offspring exhibit a striking variation in lifespan. Significantly, the hybrid strains tested either exhibited lifespans that are identical to the parental K6001 or, alternatively, threefold lower. The data clearly shows that differences among lifespans of hybrid offspring can be efficiently quantified using the DEAD assay.

Example 6

Screening Library of Nonessential Gene Deletions Using DEAD Assay

A systematic analysis of ~4800 nonessential yeast genes for roles in lifespan is made feasible by the *S. cerevisiae* Genome Deletion Project. The *Saccharomyces* Genome Project has revealed the presence of approximately 6000 open reading frames ("ORFs") in the *S. cerevisiae* genome, approximately one third of which currently have no known function four years after their discovery. As part of the deletion process, each gene disruption was replaced with a KanMX module and uniquely tagged with one or two 20mer sequence(s). Nearly all ORFs larger than 100 codons have been disrupted; highly similar ORFs were not attempted (~3%). Four different mutant collections have been generated: haploids of both mating types, homozygous diploids for non-essential genes, and heterozygous diploids, which contain the essential and non-essential ORFs. Initial results reported by *S. cerevisiae* Genome Deletion Project suggest that 18.7% of the genes are essential for growth on rich glucose media and approximately 15% of the homozygous diploid disruptions cause slow growth in this type of media.

Strain K6001, which bears a pair of separate and distinct DEAD transgenes [GAL1::CDC6 and HO::CDC6], is in a W303 genetic background that is distinct from the BY/FY backgrounds used to sequence the yeast genome and construct the deletion library, although both are derived from S288C (Rogowska-Wrzensinska et al., "Comparison of the Proteome of Three Yeast Wild Type Strains: CEN.PK2, FY1679, and W303," *Comparative and Functional Genomics,* 2:207-225 (2001)). Since most of the query strains tested to date are also in a BY background, it is necessary to transfer the GAL1::CDC6 and HO::CDC6 loci from the K6001 cells into a standard BY3656 query strain. It has already been demonstrated that the strain mates and sporulates well when crossed to the deletion library (see Example 5). This can be done in a straightforward fashion by directed replacement or standard backcrossing, because the [GAL1::CDC6 GAL1::CDC6] cassette contains a URA3 auxotrophic marker that was used in the original strain construction (Bobola et al., "Asymmetric Accumulation of Ash1p in Postanaphase Nuclei Depends on a Myosin and Restricts Yeast Mating-Type Switching to Mother Cells," *Cell* 84:699-709 (1996), which is hereby incorporated by reference in its entirety). As an alternative approach, a new DEAD cassette will be prepared using CDC6 or another gene encoding an essential protein, and then transferred into a BY yeast strain (see Example 7 below).

The library will be generated using Synthetic Genetic Array ("SGA") Analysis developed by the Boone laboratory (Toronto, Canada). The SGA Analysis is based on a clever strategy for performing huge synthetic lethal screens (Tong et al., "Systematic Genetic Analysis with Ordered Arrays of Yeast Deletion Mutants," *Science* 294:2364-2368 (2001), which is hereby incorporated by reference in its entirety). Basically, systematic construction of double mutants is performed using a query mutation crossed to an array of ~5000 deletion mutants. The SGA system automates yeast genetic analysis, allowing genetic manipulations on an unprecedented scale. Multiple (e.g. triplicate) independently produced copies of the ~4800 strain DEAD library will be produced on YPGal medium by a robot and tested separately to control for variation and nonsystematic errors in the protocol.

To test for the artifactual presence of diploids in the resultant DEAD knock-out library, which will contain a wild type CDC6 gene and therefore will produce colonies on glucose, two steps will be performed. First, production of the library in triplicate will identify those diploid contaminants following replica-pinning the triplicate libraries onto both galactose and glucose-containing media. Second, manual growth curve analysis will be performed on a number of strains containing deletions of known aging and non-aging genes, and duplicate strains produced by the SGA Analysis will be tested for possible clone-specific variation in lifespan in glucose.

Example 7

Construction of a New DEAD Cassette

K6001 is a complicated strain of indeterminate history. The native CDC6 gene was apparently replaced with an entirely new GAL1::CDC6 gene, and the HO gene was disrupted by insertion of a second CDC6 downstream of the promoter (Bobola et al., "Asymmetric Accumulation of Ash1p in Post-anaphase Nuclei Depends on a Myosin and Restricts Yeast Mating-Type Switching to Mother Cells," *Cell* 84:699-709 (1996), which is hereby incorporated by reference in its entirety). The K6001 DEAD cassette involves changes at two distinct chromosomal loci which segregate independently.

A DEAD cassette based on a URA3 CEN plasmid will be prepared and can be introduced by transformation into a cdc6Δ BY strain. The URA3 marker will be used to select for the plasmid in the ura3 auxotrophic BY strain background, and the CEN origin will maintain the plasmid at a low copy number. The chromosomal HO gene need not be disrupted. This plasmid will encode both GAL1/10::CDC6 and HO::CDC6 genes. The sequences of the Gal1/10 promoter, the HO promoter, and cytochrome c transcription terminator are identified above as SEQ ID NOS: 1-3. The cdc6 nucleotide sequence is presented as SEQ ID NO: 4 below:

```
atgtcagcta taccaataac tccaactaag cgtatcagaa gaaatctatt tgacgatgct   60
ccagcaacgc ctccacgacc tttgaaaaga aaaaagttgc agttcacaga tgttacacca  120
gaatcatccc cagaaaaact gcagtttggc tcacagtcta tttttttgag gacaaaggca  180
cttttgcaga agtcatctga gctagtcaac ttgaatagca gcgatggtgc attgccagca  240
agaacagcag agtacgaaca agttatgaat ttttggcga aggcaatttc tgaacacagg  300
tccgattcac tgtacatcac gggtccgcct ggcactggca agactgccca gcttgatatg  360
attataagac agaagttcca gtccctccca ttgtcgctct ccacgccacg ctcgaaggac  420
gtgctgagac atacgaatcc gaacttgcag aatttgtcct ggtttgaatt gcccgatgga  480
aggctagaat ccgtggcggt aaccagtatt aattgtatat cgttgggaga gccgtcctcc  540
attttccaga agattttcga ttccttccaa gatctgaatg gcccaacatt gcaaataaaa  600
aacatgcagc atctacagaa gttcttagag ccttatcata agaaaactac gtttgtggtt  660
gtgttggacg agatggacag gctattgcat gctaacacga gcgagacaca atcagttaga  720
actattcttg aattattcct tttggcgaaa ttgcctactg tgagtttgt gttaatcggt  780 atggctaata gtctagatat gaaagatagg tttctttcca ggttaaattt ggacagaggg  840
ttgttaccgc aaactatagt ttttcagcca tacactgctg agcaaatgta tgaaatcgtc  900
attcaaaaaa tgagtagtct gcccactatt atcttccaac cgatggccat caaattcgca  960
gcaaagaagt gtgctggaaa tacgggtgac cttcgaaaac tttttgatgt cttaagggga 1020
agtatcgaaa tctatgagtt agaaaagcgg tttctgcttt caccaacaag aggatcattg 1080
aactctgcgc aagttccttt gacgccaact acttctccgg taaagaaatc gtatccagaa 1140
ccacaaggta aaataggctt gaactacata gccaaggtct tctcaaaatt cgtgaacaat 1200
aattctacga gaacgaggat agccaaacta aacatccagc aaaaattaat tctttgcacc 1260
ataattcaat cactgaagct aaattccgat gctacaatcg acgaatcgtt tgatcattat 1320
atcaaagcga taacaaaaac tgatacttta gcaccattgc agagaaatga attttggaa 1380 atctgtacaa ttttagaaac ttgtgggctg gtttcaatca aaaagacaaa gtgtaaaggg 1440
aaaaccaaga gatttgttga taagattgat gttgatctcg acatgcgaga attttatgat 1500
gagatgacca aaatttcaat tttgaaacct ttccttcact ag                    1542
```

The plasmid can be introduced into a CDC6 cdc6Δ heterozygous diploid strain, and cdc6Δ haploid strains containing the plasmid will be obtained by sporulation and growth in galactose, such that the strain will be maintained by Cdc6 expressed from the GAL1::CDC6 gene on the plasmid.

This strain will be particularly useful for crossing with the entire deletion strain library (identified in Example 6) in SC drop-out media that selects both for expression of GAL1:: CDC6 and URA3 from the plasmid. Alternatively, the two genetic elements of the DEAD cassette will be integrated into the chromosome(s) of the host strain, preferably at one locus (e.g., in tandem at the CDC6 locus).

Since these strategies are not limited to the use of the CDC6 gene, it will be used to explore the advantages and disadvantages of alternative cell cycle genes. Cell cycle (cdc) genes were originally defined by conditional mutations that cause arrest under restrictive conditions with a uniform terminal morphology (reviewed in Lew et al., "Cell Cycle Control in *S. cerevisiae*," In: *The Molecular and Cellular Biology of the Yeast Saccharomyces* (eds. Pringle, Broach, Jones) Cold Spring Harbor Press, pp. 607-695 (1997), which is hereby incorporated by reference in its entirety). These genes fall into functionally different categories. Some encode proteins that are important for the sequential progression of the cell cycle "clock". These include CDC4, CDC34, CDC53, CDC16, CDC23, CDC23, CDC26, and CDC27. Others encode proteins that are important for processes (like DNA replication) that are monitored by cell cycle checkpoints. These include CDC6, CDC2, CDC7, CDC8, CDC9, CDC13, etc. Finally there are genes that encode factors involved in the morphogenetic steps of the cell cycle, such as bud formation, spindle body replication, cytokinesis, and organelle inheritance. These include CDC24, CDC42, CDC3, CDC10, and MDM2. Others, such as CDC20 mutants, have been widely used to efficiently arrest the cell cycle at G2/M, and CDC28 is required for passage through both G1/S and G2/M phases. These should likewise prove useful in formation of alternative DEAD cassettes. A successful DEAD gene product should have a short half-life so that it disappears as quickly as possible from daughter cells. The half-lives of many Cdc proteins have been quantified, and many of the "destruction boxes" or "PEST" sequences that mediate turnover have been characterized. Clb2, for example, has a half-life of less than 1 min (Amon et al., "Closing the Cell Cycle Circle in Yeast: G2 Cyclin Proteolysis Initiated at Mitosis Persists Until the Activation of G1 Cyclins in the Next Cycle," *Cell* 77(7):1037-1050 (1994), which is hereby incorporated by reference in its entirety). We will also construct hybrid DEAD genes by fusing more efficient degradation signals to those with other strong characteristics (e.g., providing a tight arrest phenotype).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of identifying a gene that alters the lifespan of an organism, said method comprising:

providing a control cell culture and one or more test cultures each comprising mother and daughter cells possessing two chimeric genes encoding a protein required for replication, one gene under control of an inducible promoter responsive to growth medium conditions and the other gene under control of a promoter operable in mother cells but not daughter cells; wherein one or more test cell cultures but not the control cell culture comprise mother yeast cells that possess a genotype modification of either a non-essential gene or an essential gene, in which case the genotype modification is non-lethal;

culturing the control cell cultures and one or more test cell cultures under conditions whereby mother yeast cells can replicate and daughter yeast cells cannot; and determining whether the mother yeast cells in the one or more test cell cultures exhibit a change in replicative lifespan when compared to the mother yeast cells in the control cell culture, wherein an increase in the replicative lifespan for mother yeast cells of a test cell culture indicates that the genotype modification enhances the replicative lifespan of an organism possessing the genotype modification and a decrease in the replicative lifespan for mother yeast cells of a test cell culture indicates that the genotype modification decreases the replicative lifespan of an organism possessing the genotype modification;

wherein the yeast strain is a homozygous diploid host strain of yeast carrying two identical copies of each of the two chimeric genes but having a mutation in one copy of the non-essential gene.

2. A method of identifying a gene that alters the lifespan of an organism, said method comprising:

providing a control cell culture and one or more test cultures each comprising mother and daughter cells possessing two chimeric genes encoding a protein required for replication, one gene under control of an inducible promoter responsive to growth medium conditions and the other gene under control of a promoter operable in mother cells but not daughter cells; wherein one or more test cell cultures but not the control cell culture comprise mother yeast cells that possess a genotype modification of either a non-essential gene or an essential gene, in which case the genotype modification is non-lethal;

culturing the control cell cultures and one or more test cell cultures under conditions whereby mother yeast cells can replicate and daughter yeast cells cannot, said culturing being carried out on a solid growth medium; and determining whether the mother yeast cells in the one or more test cell cultures exhibit a change in replicative lifespan when compared to the mother yeast cells in the control cell culture, wherein an increase in the replicative lifespan for mother yeast cells of a test cell culture indicates that the genotype modification enhances the replicative lifespan of an organism possessing the genotype modification and a decrease in the replicative lifespan for mother yeast cells of a test cell culture indicates that the genotype modification decreases the replicative lifespan of an organism possessing the genotype modification;

said determining comprising assessing colony size of colonies present in the control cell culture and colonies present in the one or more test cell culture, said assessing comprising capturing an image of colonies present in the control cell culture and an image of each of the one or more test cell cultures; and calculating the two-dimensional area of colonies in each of the images, wherein the two-dimensional area of a colony is proportional to the replicative lifespan of the mother cell.

3. The method according to claim 2 wherein said culturing is carried out in a growth medium that allows for mother cell replication but not daughter cell replication.

4. The method according to claim 3 wherein the growth medium of the control cell culture and the one or more test cell cultures is free of galactose.

5. The method according to claim 2 wherein the one or more test cell cultures comprise mother cells that possess a genotype modification involving a nonessential gene.

6. The method according to claim 2 wherein the one or more test cell cultures comprises greater than ten test cell cultures.

7. The method according to claim 2 wherein the one or more test cell cultures comprises greater than one-hundred test cell cultures.

8. A method of identifying a gene that alters the lifespan of an organism, said method comprising:

providing a control cell culture and one or more test cultures each comprising mother and daughter cells possessing two chimeric genes encoding a protein required for replication, one gene under control of an inducible promoter responsive to growth medium conditions and the other gene under control of a promoter operable in mother cells but not daughter cells; wherein one or more test cell cultures but not the control cell culture comprise mother yeast cells that possess a genotype modification of a non-essential gene, which genotype modification is selected from the group of a deletion mutant, an overexpression mutant, an addition mutant, or encoding a mutant protein;

culturing the control cell cultures and one or more test cell cultures under conditions whereby mother yeast cells can replicate and daughter yeast cells cannot; and determining whether the mother yeast cells in the one or more test cell cultures exhibit a change in replicative lifespan when compared to the mother yeast cells in the control cell culture, wherein an increase in the replicative lifespan for mother yeast cells of a test cell culture indicates that the genotype modification enhances the replicative lifespan of an organism possessing the genotype modification and a decrease in the replicative lifespan for mother yeast cells of a test cell culture indicates that the genotype modification decreases the replicative lifespan of an organism possessing the genotype modification.

* * * * *

UNITED STATES PATENT AND TRADEMARK OFFICE
CERTIFICATE OF CORRECTION

| | | |
|---|---|---|
| PATENT NO. | : 7,618,774 B2 | Page 1 of 1 |
| APPLICATION NO. | : 10/790456 | |
| DATED | : November 17, 2009 | |
| INVENTOR(S) | : Goldfarb et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 959 days.

Signed and Sealed this

Fourteenth Day of December, 2010

David J. Kappos
*Director of the United States Patent and Trademark Office*